United States Patent [19]

Ramachandran et al.

[11] Patent Number: 5,262,547
[45] Date of Patent: * Nov. 16, 1993

[54] PROCESS FOR THE PRODUCTION OF PETROCHEMICALS

[75] Inventors: Ramakrishnan Ramachandran, Allendale; Arthur I. Shirley, Piscataway; Lien-Lung Sheu, Scotch Plains, all of N.J.

[73] Assignee: The BOC Group, Inc., New Providence, N.J.

[ * ] Notice: The portion of the term of this patent subsequent to Jun. 30, 2009 has been disclaimed.

[21] Appl. No.: 772,948

[22] Filed: Oct. 15, 1991

Related U.S. Application Data

[63] Continuation-in-part of Ser. No. 607,198, Oct. 31, 1990, Pat. No. 5,126,463.

[51] Int. Cl.$^5$ .................. C07D 307/33; C07D 307/89
[52] U.S. Cl. ..................................... 549/262; 549/247; 549/248; 549/249; 549/250; 549/256; 558/318; 558/320; 558/327; 558/330; 562/545; 568/476; 568/910; 568/469.9; 570/224; 570/243; 570/248; 570/251

[58] Field of Search .................. 549/256–262, 549/248, 249, 250, 247; 558/318, 320, 327, 330; 562/545; 568/476, 513, 910; 570/224, 243, 248, 251

[56] References Cited

U.S. PATENT DOCUMENTS

| | | | |
|---|---|---|---|
| 3,904,652 | 9/1975 | Frank | 549/259 |
| 4,231,943 | 11/1980 | Paradis et al. | 549/259 |
| 4,352,755 | 10/1982 | Higgins et al. | 549/258 |
| 4,987,239 | 1/1991 | Ramachandran et al. | 549/262 |
| 5,045,297 | 9/1991 | Bonifaz et al. | 523/247 |

*Primary Examiner*—Cecilia Tsang
*Attorney, Agent, or Firm*—Coleman R. Reap; Larry R. Cassett

[57] ABSTRACT

Petrochemicals are produced by the vapor phase reaction of a hydrocarbon with substantially pure oxygen in the presence of a suitable catalyst. In the improved process, the principal product is removed, carbon monoxide, present in the reactor effluent as a byproduct, is oxidized to carbon dioxide and part of the gaseous effluent, comprised mainly of carbon dioxide and unreacted hydrocarbon, is recycled to the reactor. Removal of carbon monoxide from the recycle stream reduces the hazard of a fire or explosion in the reactor or associated equipment. The use of carbon dioxide as the principal diluent increases heat removal from the reactor, thereby increasing the production capacity of the reactor.

34 Claims, 1 Drawing Sheet

PROCESS FOR THE PRODUCTION OF PETROCHEMICALS

RELATED APPLICATION

This is a continuation-in-part of U.S. patent application Ser. No. 07/607,198, filed Oct. 31, 1990 U.S. Pat. No. 5,126,463.

FIELD OF THE INVENTION

The present invention is directed to a process for producing petrochemicals from a hydrocarbon and an oxygen-containing gas in the presence of a suitable catalyst, and more particularly to a process for achieving increased production while reducing or eliminating the hazard of an explosion or fire in an existing or new vapor phase reactor system in which a petrochemical is produced from a hydrocarbon and oxygen.

BACKGROUND OF THE INVENTION

Certain petrochemicals are produced commercially by the partial oxidation of an appropriate hydrocarbon in the vapor phase over a suitable catalyst and in the presence of an oxygen-containing gas. For example, cyclic anhydrides are produced commercially by the vapor phase catalytic partial oxidation of aromatic hydrocarbons, such as o-xylene or benzene, or straight-chain hydrocarbons, such as n-butane, or butene, in the presence of an oxygen-containing gas, over a vanadium-containing catalyst. Similarly, nitriles, alkylene oxides, aldehydes and halogenated hydrocarbons are produced by the partial oxidation of appropriate alkanes and alkenes in the presence of selected catalysts. Air is generally used as the oxygen-containing gas, because of its low cost and ready availability. The reaction can be carried out in any suitable reactor, such as a fixed bed, fluidized bed, moving bed, trickle bed or transport bed reactor, and it produces the petrochemical, and generally carbon monoxide (CO), carbon dioxide ($CO_2$), water, and smaller amounts of other partially oxidized by-products. The reaction equipment train generally consists of a reactor, in which the petrochemical product is produced, a scrubber, in which the petrochemical product is scrubbed from the reactor effluent gases by means of water or other solvent for the petrochemical, and means for further treating the scrubbed effluent gases.

In the past it was common to practice the above-described process on a single pass basis with the conversion of hydrocarbon to the desired petrochemical product being maximized. This resulted in a low overall efficiency, since the selectivity to petrochemical product was below the maximum. Consequently, the scrubber effluent gas contained considerable amounts of CO and $CO_2$, in addition to unreacted hydrocarbon. These products were usually incinerated, so that the only return realized from them was heat value. In later processes a portion of the scrubber effluent gas was recycled, the conversion of the hydrocarbon feedstock was lowered and the selectivity of hydrocarbon conversion to the desired petrochemical product was increased. The remainder of the effluent was purged from the system to prevent the build-up of CO, $CO_2$ and nitrogen (introduced into the system when air is used as the source of oxygen). These improvements resulted in a reduced "per pass" conversion, but the overall efficiency of the process was increased.

Federal Republic of Germany (FRG) Patent Application Disclosure 25 44 972 discloses a maleic anhydride manufacturing process in which the reactor feed comprises $C_4$ hydrocarbons, air, CO and $CO_2$. In the process of this patent, maleic anhydride is recovered from the reactor effluent gas stream and a portion of the remaining stream is recycled. This patent also teaches recovering butane by temperature swing adsorption from the non-recycled gas stream and recycling the recovered butane to the reactor.

U.S. Pat. No. 4,352,755 discloses a recycle process for the vapor phase manufacture of maleic anhydride by reacting a straight-chain $C_4$ hydrocarbon with oxygen in the presence of $CO_2$. In the process disclosed in this patent the gaseous mixture may contain up to 30 volume percent of carbon dioxide as the inert diluent and contains at least 25 volume percent $C_4$ hydrocarbon.

Recycling a portion of the effluent gas from gas phase hydrocarbon partial oxidation reactors increases the capital costs compared to single pass processes since the size of the reactor and associated equipment must be increased to handle the increased volumes of CO, $CO_2$ and nitrogen resulting from the recycling step. The problem is intensified when low heat capacity gases such as nitrogen are used as diluents because greater gas flows are necessary to provide adequate heat removal to prevent reactor overheating.

Another problem associated with the gas phase production of a petrochemical by the oxidation of hydrocarbons with an oxygen-containing gas is that since the reaction is carried out at elevated temperatures, there is an ever-present danger of a fire or an explosion in the reactor or the equipment or pipelines associated with the reactor. Accordingly, the concentrations of the reactants in the system are maintained such that the mixture is kept outside of the flammability range. Although nitrogen serves to reduce the flammable mixture range when air is used as the source of oxygen for the reaction, the flammable mixture range for hydrocarbon-air mixtures is still quite broad. Consequently, it has been customary to operate gas phase hydrocarbon oxidation reactors at low hydrocarbon levels so that the reaction mixture will remain outside of the flammable range.

U.S. Pat. No. 4,231,943 discloses the production of maleic anhydride by the reaction of n-butane and air in the presence of a catalyst comprising vanadium and phosphorus oxides. The process of this patent includes the steps of recovering maleic anhydride from the gaseous oxidation reactor effluent, directly recycling a portion of the maleic anhydride-free effluent to the reactor, separating relatively pure n-butane from the remaining gaseous effluent and recycling the relatively pure n-butane to the feed stream.

U.S. Pat. No. 3,904,652 teaches a gas phase maleic anhydride manufacturing process in which oxygen is used as the oxidizing gas and an inert gas, such as nitrogen, argon, helium or a lower hydrocarbon is fed into the reactor with the n-butane and oxygen, the inert gas serving as a diluent to reduce the concentrations of oxygen and butane in the reactor to below the point at which they form a flammable mixture. In the disclosed process, a portion of the gaseous effluent, which contains, in addition to butane, carbon monoxide, carbon dioxide and the inert gas, is recycled. One of the disadvantages of a process such as the one disclosed in this patent is that recycling carbon monoxide increases the fire and explosion hazard because carbon monoxide itself is highly flammable.

U.S. Pat. No. 4,352,755 discloses a recycle process for the vapor phase manufacture of maleic anhydride by reacting a straight-chain $C_4$ hydrocarbon with oxygen in the presence of $CO_2$. In the process disclosed in this patent the gaseous mixture may contain up to 30 volume percent of carbon dioxide as the inert diluent and contains at least 25 volume percent $C_4$ hydrocarbon. This patent states that at most 2% v/v and more preferably at most 1% v/v of carbon monoxide is present in the oxidation stage. In the process of this patent, the presence of large amounts of $C_4$ hydrocarbon can render the gas mixture in the system flammable.

U.S. Pat. No. 4,987,239 discloses a process for the production of anhydrides by the reaction of hydrocarbons with an oxygen-containing gas in the presence of a suitable catalyst. In the process of this patent, a selective separator provides recycle of a substantial portion of the unreacted hydrocarbon and a controlled amount of a gaseous flame suppressor.

Because of ever increasing safety concerns and energy costs, there are continuing efforts by industry to make chemical processes involving oxygen and flammable compounds less hazardous and more economical to operate. This invention presents a process which provides these advantages.

SUMMARY OF THE INVENTION

The present invention provides an improvement in a recycle process for manufacturing petrochemicals, such as nitrile, alkylene oxide, halogenated hydrocarbon and aldehyde petrochemicals by the oxidation of selected hydrocarbons with oxygen in the presence of suitable catalysts. In such a process the reactor effluent contains the petrochemical as the main product, carbon monoxide and carbon dioxide as by-products and, in most cases, unreacted hydrocarbon. The invention includes the step of converting some or all of the carbon monoxide in the effluent stream to carbon dioxide by contacting it with an appropriate oxidation catalyst, and recycling a portion of the carbon dioxide with the unreacted hydrocarbon.

According to one aspect of the process of the invention, one or more hydrocarbons are contacted with an oxygen-containing gas, preferably in the vapor phase, in a suitable oxidation reactor and in the presence of carbon dioxide as a diluent, preferably as the principal diluent, to produce a gaseous product stream containing the petrochemical, the specific petrochemical product produced depending upon which alkanes and/or alkenes are reacted, the particular catalyst used and, in some cases, the presence of other reactants. The hydrocarbon oxidation reactor product stream also contains carbon monoxide and carbon dioxide, and generally unreacted hydrocarbon(s), oxygen, inert gases, if any, introduced into the reactor and possibly small amounts of other reaction by-products. The gaseous product stream leaving the oxidation reactor is then introduced into a petrochemical removal means, which, for example, may be a condenser or a scrubber in which it is contacted with a liquid solvent which removes substantially all of the petrochemical product from the gas stream. The petrochemical product is recovered from the product removal means as a liquid or solid. Prior to or following the petrochemical removal step all or a portion of the gaseous product stream is treated in a carbon monoxide converter to convert some or all of the carbon monoxide in the stream to carbon dioxide. In the preferred embodiment, a catalyst is selected which oxidizes the carbon monoxide without oxidizing the unreacted hydrocarbon present in the stream to any great extent. Part of the carbon dioxide is subsequently removed from the stream and the remainder of the stream is recycled to the hydrocarbon oxidation reactor.

In a preferred embodiment of the process aspect of the invention the oxygen-containing gas is substantially pure oxygen and the principal diluent in the system is carbon dioxide. In another preferred embodiment the concentration of carbon dioxide present in all parts of the reaction system is sufficiently high to alone prevent the formation of a flammable mixture in the system. In yet another preferred embodiment the hydrocarbon oxidation step is carried out in a fixed bed reactor. In another preferred embodiment the hydrocarbon reactant contains 2 to 12 carbon atoms; in a more preferred embodiment the hydrocarbon is selected from alkanes and alkenes having 2 to 12 carbon atoms; and in the most preferred embodiment, the hydrocarbon is selected from alkanes and alkenes having 2 to 6 carbon atoms. In other preferred embodiments carbon dioxide is removed from the gaseous product stream by purging, adsorption or absorption.

DETAILED DESCRIPTION OF THE INVENTION

Figure 1:
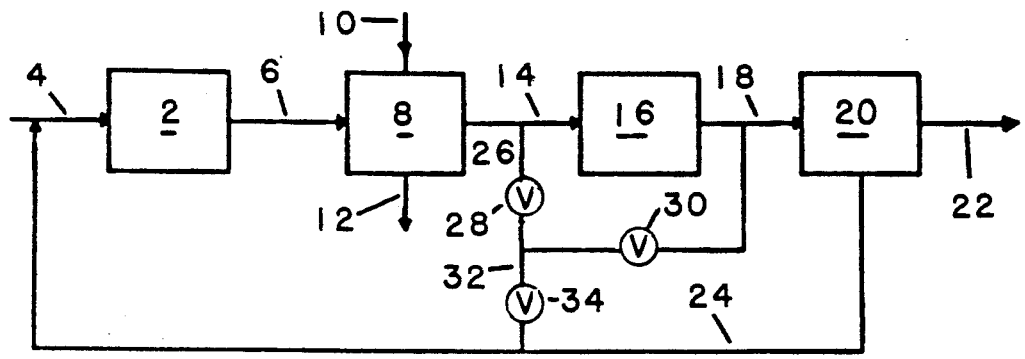
FIG. 1 illustrates, in a block diagram, a system for producing a petrochemical product in accordance with one embodiment of the present invention.

The process of the invention can be used for the manufacture of any petrochemical that is produced by the gas phase reaction at elevated temperatures of a hydrocarbon with oxygen. Typical petrochemical manufacturing processes in which the invention can be employed are:

1. The manufacture of cyclic anhydrides by the reaction of aromatic compounds or straight-chained $C_4$ hydrocarbons with oxygen in the presence of a vanadia-based catalyst. Examples include the production of maleic anhydride by the reaction of benzene or a saturated or unsaturated $C_4$ hydrocarbon with oxygen and the manufacture of phthalic anhydride by the reaction of o-xylene or naphthalene with oxygen.

2. The manufacture of an olefinically unsaturated nitriles by the reaction of lower alkanes or alkenes with oxygen and ammonia in the presence of a bismuth molybdenum oxide catalyst or an iron antimony oxide catalyst mounted on a silica or alumina support. Examples of this type of process include the reaction of propane or propylene with oxygen and ammonia to produce acrylonitrile and the reaction of i-butane or i-butylene with oxygen and ammonia to produce methacrylonitrile.

3. The manufacture of alkylene oxides by the reaction of lower alkanes or alkenes with oxygen in the presence of a silver oxide catalyst mounted on a silica or alumina support or mixed molten nitrate salts. Examples include the reaction of ethane or ethylene with oxygen to produce ethylene oxide and the reaction of propane or propylene with oxygen in the presence of molten sodium and potassium nitrates to produce propylene oxide.

4. The manufacture of chlorinated hydrocarbons by the reaction of lower alkanes or alkenes with oxygen in the presence of a copper chloride catalyst supported on silica or alumina. Examples include the reaction of ethylene or ethane with hydrogen chloride or chlorine to produce vinyl chloride or ethylene dichloride.

5. The manufacture of aldehydes by the reaction of lower alkanes or alkenes with oxygen in the presence of various metal halides or metal oxide catalysts. Examples include the production of acetaldehyde by the reaction of ethylene with oxygen in the presence of copper chloride and palladium chloride, and the manufacture of acrolein by the reaction of propylene with oxygen over a molybdenum-bismuth-iron catalyst.

As is apparent from the above examples, the process of the invention can be used for the manufacture of various petrochemicals in the above-mentioned classes by the reaction of appropriate hydrocarbons with oxygen. The particular partial oxidation reaction that is carried out in the process of the invention is not critical to the invention. In general, the process of the invention can include any hydrocarbon oxidation reaction that is carried out in the vapor phase at elevated temperatures to produce any of the above petrochemicals and which involves the reaction of a hydrocarbon and oxygen (and, where appropriate, other reactants, such as ammonia, hydrogen chloride or chlorine) in the presence of a catalyst to produce the petrochemical as the main product and carbon dioxide and carbon monoxide as by-products.

The particular hydrocarbon or hydrocarbons used as reactant in the hydrocarbon oxidation step of the process of the invention will be determined by the particular petrochemical that is being produced. In general, the feed hydrocarbon may be aromatic, aliphatic or cycloaliphatic, and it may be saturated or ethylenically unsaturated and straight chain or branched. Suitable aromatic hydrocarbons include those having up to twelve or more carbon atoms and suitable aliphatic and cycloaliphatic hydrocarbons include those having two to twelve or more carbon atoms. Preferred aromatic hydrocarbons are those having six to ten carbon atoms, such as benzene, o-xylene and naphthalene, and preferred aliphatic hydrocarbons are the saturated or ethylenically unsaturated straight-chain hydrocarbons having two to six hydrocarbon atoms, such as ethane, ethene, propane, propylene, n-butane, i-butane, n-butylene, i-butylene, butadiene, and the pentanes, pentenes, hexanes and hexenes.

Oxygen sources useable in the process may be pure oxygen or oxygen-containing gases, such as air, oxygen-enriched air or other oxygen-inert gas mixtures. By oxygen-enriched air is meant air that contains more oxygen than is naturally present in air. Oxygen-inert gas mixtures include oxygen-nitrogen mixtures, oxygen-argon mixtures, oxygen-carbon dioxide mixtures, etc. Pure oxygen is preferred since its use avoids the introduction of excess inert gases, such as nitrogen and argon, into the system and the subsequent need to remove excess quantities of these inert gases from the product gas stream to prevent their buildup in the system.

The invention can be better understood from the accompanying drawings, in which the same reference numeral is used to designate the same or similar equipment in the various figures. Auxiliary equipment, including valves, compressors and heat exchangers, which are unnecessary for an understanding of the invention have been omitted from the drawings to simplify discussion of the invention.

Considering first FIG. 1, the apparatus of this embodiment includes a hydrocarbon partial oxidation reactor 2 having a feed inlet means 4 and a product outlet 6. Product outlet 6 is connected to a petrochemical product recovery unit such as scrubber 8, which receives a scrubbing liquid through inlet 10 and discharges a liquid product through outlet 12. Scrubber 8 is also equipped with a scrubbed gas outlet 14 which communicates with carbon monoxide converter 16. Converter 16 discharges oxidized gas through line 18, which is connected to carbon dioxide separator 20. Separator 20 is provided with a waste gas discharge line 22, and it is also connected via recycle line 24 with feed inlet means 4. The system illustrated in FIG. 1 is also equipped with a bypass line 26, controlled by valves 28 and 30, and bypass line 32, controlled by valve 34.

Figure 2:
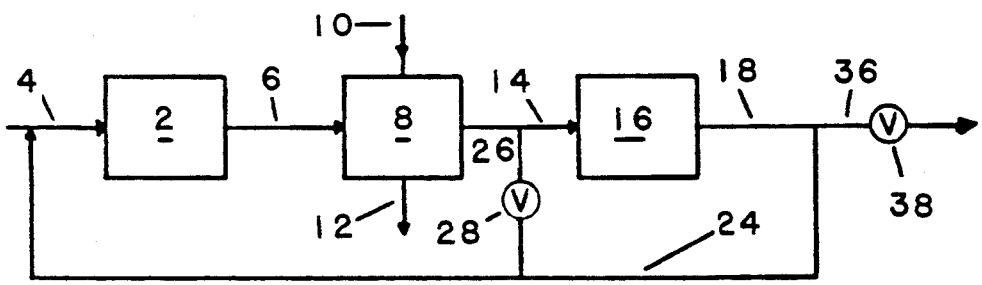
FIG. 2 illustrates, in a block diagram, a system for producing a petrochemical product in accordance with a second embodiment of the invention.

FIG. 2 illustrates a variation of the system of FIG. 1. This system is substantially the same as the FIG. 1 system, however in the FIG. 2 system the carbon dioxide separator 20 of FIG. 1 is replaced by a purge line 36 which is controlled by valve 38.

Figure 3:
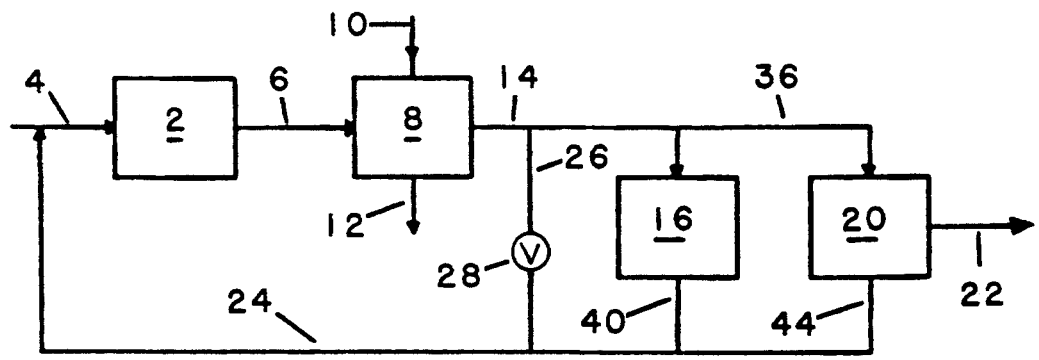
FIG. 3 illustrates, in a block diagram, a modified embodiment of the system illustrated in FIG. 1.

FIG. 3 illustrates another variation of the system of FIG. 1. In the embodiment of FIG. 3, carbon monoxide converter 16 and carbon dioxide separator 20 are arranged in parallel and each of these units can receive as feed a portion of the effluent from scrubber 8. Converter 16 receives scrubber effluent via line 14 and discharges oxidized gas for recycle to reactor 2 via lines 40 and 24; and separator 20 receives scrubber effluent via lines 14 and 36 and discharges a waste stream to vent through line 22 and a stream for recycle to reactor 2 via lines 44 and 24. The system of FIG. 3 is also equipped with a bypass line 26, controlled by valve 28. Flow through converter 16, separator 20 and bypass line 26 can be adjusted to any desired rates.

Reactor 2 may be any suitable reactor but it is usually of the fixed, moving, fluidized, trickle or transport catalyst bed design. The invention is particularly effective when the petrochemical products are produced in fixed bed reactors because of the significantly higher heat build-up in this type of reactor. Reactor 2 may be equipped with heat exchange means to remove heat developed in the reaction, which is exothermic. The specific design details of suitable reactors are well known and they form no part of the present invention. Petrochemical product recovery unit 8 is typically a conventional gas scrubber, i.e. an absorber, usually of the packed bed design, and it is here illustrated as equipped with means for spraying water or an aqueous or nonaqueous liquid on the product gas entering this unit from reactor 2. Converter 16, like reactor 2, may be of any suitable design. In preferred embodiments of the invention converter 16 is a fixed bed reactor. Although converter 16 is positioned downstream of the petrochemical product scrubber in the drawings, it can be located upstream of the petrochemical product scrubber, or, if desired, it can even be incorporated in reactor 2. The purpose of carbon dioxide separator 20 is to remove carbon dioxide and other inert gases from the system, and this unit can be any device which will accomplish this result. Separator 20 is usually an adsorber or an absorber. In preferred embodiments of the invention separator 20 is a pressure swing adsorption (PSA) unit or a temperature swing adsorption (TSA) unit.

In the process of the invention, feed, comprising a suitable hydrocarbon, an oxygen-containing gas, other reactants, where appropriate, and the recycle gas stream, enters reactor 2 through inlet means 4, which may comprise a single inlet line through which a mixture of the gaseous reactants and diluents is introduced into reactor 2, or it may comprise several individual inlet lines for separately introducing the reactants into the reactor. The particular inlet arrangement will generally depend upon the type of reactor used for practicing the invention. In fixed bed reactor systems the components of the feed are generally mixed before they enter the reactor and are thus fed into the reactor through a single line, whereas in fluidized bed reactor systems, the components are usually separately fed into the reactor.

It can be appreciated that to fully realize the main benefit of the invention, i.e. the oxidation of carbon monoxide to carbon dioxide, carbon dioxide must be recycled as a diluent in the system. In the preferred embodiment carbon dioxide is present in the system as the principal inert diluent, i.e. carbon dioxide is present in the reaction system at a concentration greater than any other inert gaseous component. Thus, other inert gaseous components, such as nitrogen, argon, water vapor and nonreactive compounds, including nonreactive hydrocarbons, may be present in the system, but, on a volume basis, the concentration of each of these other inert components in the system is less than the concentration of carbon dioxide in the system. An "inert gaseous component" is one that does not react under the conditions existing in the system. The carbon dioxide concentration in the system is preferably maintained sufficiently high so that it alone will prevent the gases in any part of the system from forming a flammable mixture. In the preferred embodiment, carbon dioxide comprises at least 50 volume percent, and in the most preferred embodiment carbon dioxide comprises at least 70 volume percent of the total gases in the system.

In the startup operation of the process of the invention, carbon dioxide or any other inert gas can be introduced into the system with the feed to insure that the gas mixture is and remains outside of the flammable range. It is often convenient to use an inert gas other than carbon dioxide in the startup operation. For example, if air is used as the oxygen source during the startup period, the nitrogen component of the air can serve as the diluent until the carbon dioxide level increases to the desired level. Then, in the preferred embodiment, the air can be gradually replaced by substantially pure oxygen or oxygen-enriched air. The carbon dioxide can be easily maintained in the desired range by controlling the amount of carbon dioxide recycled.

The feed gases entering reactor 2 contact the catalyst and react to form the product gases. Any of the well known catalysts for partially oxidizing hydrocarbons to the desired petrochemical under the specified conditions can be used in the process of the invention. Suitable catalysts include vanadia-based catalysts for the preparation of cyclic anhydrides; multicomponent molybdate catalysts or antimony-containing catalysts for the preparation of nitriles; bismuth molybdate for the first stage and a mixed molybdenum-tungsten-vanadium catalyst for the second stage of a two-stage process for the preparation of unsaturated carboxylic acids from alkenes; and silver oxide or mixed molten nitrates for the preparation of alkylene oxides. These catalysts and their use are conventional and well known to those skilled in the manufacture of petrochemical products. The specific hydrocarbon partial oxidation catalysts used in the process of the invention do not form a part of the invention.

The conditions of the hydrocarbon partial oxidation are well known and likewise form no part of the invention. Typically, the oxidation reaction is conducted at a temperature of from about 120° to about 600° C., and usually from about 150° to about 500° C., and at pressures typically in the range of from about 2 to about 500 psig, and usually in the range of about 3 to about 350 psig. The reactants are generally passed through the reactor at a velocity in the range of from about 0.5 to about 5.0 ft/sec. The volume ratio of oxygen to hydrocarbon in the feed is suitably in the range of about 0.3:1 to about 50:1.

The product gas stream leaving reactor 2 contains the desired petrochemical as the main product, and carbon dioxide and carbon monoxide as by-products. As noted above, the product stream generally also contains unreacted hydrocarbon and oxygen, and may contain small amounts of other by-products, impurity gases and nonreactive hydrocarbons. In the embodiments illustrated in the drawings, the product gas stream leaves reactor 2 via line 6 and enters petrochemical product scrubber 8. The purpose of unit 8 is to remove the petrochemical product from the hydrocarbon reactor effluent gas. In scrubber 8 the product gases are intimately contacted with a solvent for the petrochemical product. The solvent dissolves substantially all of the petrochemical product out of the product gas stream and this solution leaves scrubber 8 via line 12. It is usually further treated to recover the petrochemical product. The scrubbed gas stream leaves scrubber 8 through line 14 and enters carbon monoxide converter 16.

The purpose of carbon monoxide converter 16 is to convert carbon monoxide produced in the hydrocarbon oxidation reaction to carbon dioxide in order to prevent the build-up of carbon monoxide in the system. Converter 16 contains a catalyst which promotes the oxidation of carbon monoxide to carbon dioxide. Any catalyst that will promote the oxidation of carbon monoxide to carbon dioxide can be used in the process of the invention. Preferred catalysts are those which oxidize carbon monoxide to carbon dioxide under conditions such that little or none of the hydrocarbon present in the gas stream entering the carbon monoxide converter is oxidized. Among the catalysts suitable for use in converter 16 are the mixed copper-manganese oxides and the noble metal catalysts, such as platinum-nickel catalyst. These compositions may be used as is or mounted on a suitable substrate, such as silica or alumina. As will become clear from the discussion which follows, the unreacted hydrocarbon and carbon dioxide leaving converter 16 are recycled to reactor 2 so that the process can be optimized. Accordingly, if carbon monoxide (which is also recycled with the unreacted hydrocarbon) is not removed, as by conversion to carbon dioxide, the concentration of carbon monoxide in the system will increase and eventually reach the level at which a flammable mixture exists. To avoid this problem, it is sufficient to remove an amount of carbon monoxide equivalent to the amount that is produced in reactor 2 in each pass. Thus, converter 16 can be a relatively small reactor.

Generally, about 1 to about 20 mole percent of the hydrocarbon entering reactor 2 is converted to carbon dioxide and about 1 to about 20 mole percent of it is converted to carbon monoxide. Since the amount of carbon monoxide converted to carbon dioxide in converter 16 is often substantially equal to the amount of carbon monoxide produced in reactor 2, the total amount of carbon dioxide produced in the reaction process is about 2 to about 40 mole percent, based on the amount of hydrocarbon entering reactor 2. Thus, it can be appreciated that an advantage of the invention is that in many cases the concentration of carbon dioxide can be quickly brought up to the desired operating level during startup.

In some cases it may not be necessary to pass all of the scrubbed gas through converter 16 to effect the desired degree of carbon monoxide conversion. In such cases a portion of the scrubbed gas effluent in line 14 can be bypassed around converter 16 through line 26 by opening valves 28 and 30 and closing valve 34 in line 32. In other cases it may be desired to permit some of the scrubbed gas in line 14 to bypass converter 16 and separator 20. In this case valves 28 and 34 are opened and valve 30 is closed. Thus, the system can be operated with all or a portion of the scrubbed gas in line 14 passing through reactor 16.

After the carbon monoxide oxidation step, the gas stream leaves converter 16 through line 18 and enters separator 20. Separator 20 serves the purpose of removing carbon dioxide and other inert gases in excess of the amounts which it is desired to recycle. For example, when air is used as the source of oxygen, carbon dioxide in excess of the amount that it is desired to recycle, nitrogen and argon are removed from the system in separator 20. To prevent the buildup of nitrogen and argon in the system when air is used as the source of oxygen, it is generally necessary to remove from the system substantially all of the nitrogen and argon entering reactor 2 with the fresh feed. This can be easily accomplished by operating separator 20 in such a manner that nitrogen and argon pass through the separator and hydrocarbon and some or all of the carbon dioxide are absorbed or adsorbed. Nitrogen, argon and excess carbon dioxide are removed from separator 20 via line 22 and the remaining carbon dioxide, unreacted hydrocarbon and a small amount of carbon monoxide are recycled to reactor 2 through line 24. Line 24 may be connected to line 4, as shown in the drawings, or it may be connected directly to reactor 2.

As indicated above, separator 20 can be any means for separating unreacted hydrocarbon and carbon dioxide from the effluent from converter 16, but in the preferred embodiment this unit is a pressure swing adsorber. Pressure swing adsorption is a well known process for separating the components of a mixture of gases by virtue of the difference in the degree of adsorption among them on a particulate adsorbent retained in a stationary bed. Typically, two or more such beds are operated in a cyclic process comprising adsorption under relatively high pressure and desorption or bed regeneration under relatively low pressure or vacuum. The desired component or components may be obtained during either of these stages. The cycle may contain other steps in addition to the fundamental steps of adsorption and regeneration, and it is commonplace to have two or more adsorbent beds cycled 180° out of phase to assure a pseudo continuous flow of desired product. While it is conventional for the adsorption step of a PSA cycle to be carried out under pressure, it can run at ambient pressure with desorption under vacuum.

In a preferred embodiment of the invention, substantially pure oxygen is used as the oxidant and carbon dioxide is used as the principal diluent gas. In this case very little or no nitrogen is introduced into the system and the gas stream entering separator 20 is comprised substantially of unreacted hydrocarbon, carbon dioxide and carbon monoxide. Separator 20 then serves to remove only a small amount of carbon dioxide from the system, and the remaining part of the gas stream entering separator 20, comprised of carbon dioxide, unreacted hydrocarbon and carbon monoxide, is recycled to reactor 2. In some cases it may not be necessary to pass all of the carbon dioxide through separator 20. In such cases part of the effluent from converter 16 can be discharged directly to recycle line 24 by opening valves 30 and 34 and closing valve 28. The system can also be operated with valves 28, 30 and 34 open, if desired.

In operating the process of the invention in accordance with the embodiment of FIG. 2, a portion of the effluent gas stream from converter 16 is purged from the system through line 36 by opening valve 38, and the remainder of the effluent is recycled to reactor 2 via line 24. Since the gas being purged has the same composition as the gas being recycled, the process of this embodiment is most convenient when the oxidant is substantially pure oxygen. In this case substantial amounts of nitrogen will not be present in the gas being recycled to reactor 2. As was the case with the FIG. 1 embodiment, a portion of the scrubbed gas leaving scrubber 8 can be bypassed around converter 16 via line 26 by opening valve 28.

In practicing the process of the invention in the system of FIG. 3, part of the effluent from scrubber 8 is passed through converter 16 to oxidize the desired amount of carbon monoxide to carbon dioxide and part of the scrubber effluent is sent to separator 20 to remove the desired amount of carbon dioxide and other inert gases, if any are present, from the system through line 22. The effluent from converter 16 (in line 40) and the stream selected for recycle from separator 20 (in line 44) are combined and returned to reactor 2 through line 24. In some situations it may not be necessary to pass all of the scrubber effluent through converter 16 and separator 20. In such cases a part of the effluent is directly recycled to reactor 2 via lines 26 and 24 by opening valve 28.

It will be appreciated that it is within the scope of the present invention to utilize conventional equipment to monitor and automatically regulate the flow of gases within the system so that it can be fully automated to run continously in an efficient manner.

Several advantages are achieved by the practice of the invention. For example, use of the carbon monoxide converter permits the process to be run without discharging carbon monoxide to the atmosphere; eliminates excess carbon monoxide from the reaction system, thereby reducing the danger of fire or explosion in the equipment used in the process; and shortens the time required to increase the carbon dioxide concentration in the system to the desired operating level. Using carbon dioxide as the inert diluent increases the production capacity of the reaction system because the relatively high heat capacity of carbon dioxide enables the reaction to be run with less inert gas present. Accordingly, the reactants can be fed to the reactor at a higher flow rate. Other advantages of the process of the invention are its simplicity, ease of operation and low capital and operating costs. Additionally, the process can be run at a relatively low per pass conversion of the feed hydrocarbon to the desired product to achieve substantially improved selectivity.

The invention is further illustrated by the following examples in which percentages, ratios, and parts, including parts per million (ppm), are on a volume basis, unless otherwise indicated.

EXAMPLE I

A gas mixture comprised of the components listed as feed in TABLE I was fed into a one-half inch carbon steel reactor containing 2 grams of mixed copper oxide-manganese oxide catalyst sold by Carus Chemical Company under the trademark Carulite* 200. The catalyst bed occupied a volume of 2.2 cc in the reactor. The gas mixture was heated to a temperature of 200° C. and was fed into the reactor at a specific flow rate of 67.6 reciprocal minutes. The results of this run are tabulated in TABLE I.

EXAMPLE II

A vapor phase maleic anhydride production run was simulated in a fixed bed reactor based on the results obtained in the experiment of EXAMPLE I. The reactor system was similar to the system of FIG. 3. The simulated feed to the hydrocarbon reactor is comprised of the Fresh Feed component and the Recycle Stream component. The reaction is simulated based on the use of a vapor phase hydrocarbon reactor containing a fixed catalyst bed of vanadium phosphorous oxide, a carbon monoxide converter containing a fixed bed catalyst comprised of Carulite* 200 and a pressure swing adsorber containing a molecular sieve adsorption bed. The various flow rates and projected results are tabulated in TABLE II.

TABLE II

| Component | Fresh Feed | | Feed to MA Reactor (1) | | Feed to MA Scrubber | | Feed to CO Convertor | | Feed to PSA | | Recycle | | Vent From PSA | |
|---|---|---|---|---|---|---|---|---|---|---|---|---|---|---|
| | Moles | Vol % | Moles | Vol % | Moles | Vol % | Moles | Vol % | Moles | Vol % | Moles | Vol % | Moles | Vol % |
| n-Butane | 78.7 | 17.9 | 141.9 | 2.4 | 63.9 | 1.1 | 25.6 | 1.1 | 38.3 | 1.1 | 63.2 | 1.2 | 0.0 | 0.0 |
| i-Butane | 3.7 | 0.8 | 6.7 | 0.1 | 3.0 | 0.1 | 1.2 | 0.1 | 1.8 | 0.1 | 3.0 | 0.1 | 0.0 | 0.0 |
| $O_2$ | 353.9 | 80.5 | 445.4 | 7.5 | 119.9 | 2.0 | 48.0 | 2.1 | 71.9 | 2.1 | 91.5 | 1.7 | 0.0 | 0.0 |
| $N_2$ | 3.5 | 0.8 | 319.2 | 5.4 | 319.2 | 5.3 | 127.7 | 5.7 | 191.5 | 5.7 | 315.7 | 5.8 | 3.5 | 2.8 |
| Maleic Anhydride | 0.0 | 0.0 | 0.0 | 0.0 | 53.2 | 0.9 | 0.0 | 0.0 | 0.0 | 0.0 | 0.0 | 0.0 | 0.0 | 0.0 |
| CO | 0.0 | 0.0 | 111.6 | 1.9 | 167.8 | 2.8 | 67.1 | 3.0 | 100.7 | 3.0 | 111.6 | 2.0 | 0.0 | 0.0 |
| $CO_2$ | 0.0 | 0.0 | 4802.7 | 81.3 | 4849.5 | 80.9 | 1939.8 | 86.3 | 2909.7 | 86.3 | 4802.7 | 87.9 | 103.6 | 82.1 |
| $H_2O$ | 0.0 | 0.0 | 76.5 | 1.3 | 418.1 | 7.0 | 38.2 | 1.7 | 57.3 | 1.7 | 76.5 | 1.4 | 19.0 | 15.1 |
| TOTAL | 439.9 | 100.0 | 5904.1 | 100.0 | 5994.6 | 100.0 | 2247.5 | 100.0 | 3371.3 | 100.0 | 5464.2 | 100.0 | 126.1 | 100.0 |

(1) Sum of Fresh Feed and Recycle

TABLE I

| | Feed | | Effluent | |
|---|---|---|---|---|
| Component | cc/min | Vol. % | cc/min | Vol % |
| $CO_2$ | 139.73 | 93.97 | 143.81 | 97.85 |
| $O_2$ | 2.77 | 1.86 | 0.51 | 0.35 |
| CO | 3.49 | 2.35 | 0.03 | 0.02 |
| $C_4H_{10}$ | 2.72 | 1.82 | 2.62 | 1.78 |
| Total | 148.70 | 100.00 | 146.97 | 100.00 |

TABLE I shows that 99.16 volume percent of the carbon monoxide fed to the reactor was converted to carbon dioxide, while the extent of the hydrocarbon conversion is minimal.

EXAMPLE III

A vapor phase acrylonitrile production run was simulated in a fixed bed reactor based on the results obtained in an experiment similar to the experiment of EXAMPLE I, but conducted at a temperature of about 300° C. The reactor system was similar to the system of FIG. 2. The simulated feed to the hydrocarbon reactor is comprised of the Fresh Feed component and the Recycle Stream component. The reaction is simulated based on the use of a vapor phase hydrocarbon reactor containing a fixed catalyst bed of bismuth molybdenum oxide, a carbon monoxide converter containing a fixed bed of Carulite* 200 catalyst. The various flow rates and projected results are tabulated in TABLE III.

Methacrylonitrile can be similarly prepared using isobutylene as the hydrocarbon reactant.

TABLE III

| Component | To Fresh Feed | | To AN Reactor | | To Quench | | TO CO Reactor | | To Recycle | | To Vent | |
|---|---|---|---|---|---|---|---|---|---|---|---|---|
| | Moles | % | Moles | % | Moles | % | Moles | % | Moles | % | Moles | % |
| $C_3H_6$ | 654.0 | 23.8 | 654.0 | 7.92 | 19.6 | 0.2 | 19.4 | 0.3 | 0.0 | 0.0 | 0.0 | 0.0 |
| $O_2$ | 1395.8 | 50.7 | 1520.7 | 18.4 | 242.2 | 2.8 | 242.2 | 4.2 | 124.9 | 2.3 | 2.5 | 2.3 |
| $N_2$ | 14.5 | 0.5 | 724.2 | 8.8 | 724.2 | 8.4 | 724.2 | 12.6 | 709.7 | 12.9 | 14.5 | 12.9 |
| $C_3H_8$ | 0.3 | 0.0 | 0.3 | 0.0 | 0.3 | 0.0 | 0.3 | 0.0 | 0.0 | 0.0 | 0.0 | 0.0 |
| $NH_3$ | 687.2 | 25.0 | 687.2 | 8.32 | 86.5 | 1.0 | | | | | | |
| AN (1) | | | | | 490.4 | 5.7 | | | | | | |
| HCN | | | | | 104.7 | 1.2 | | | | | | |
| ACR (2) | | | | | 4.4 | 0.1 | | | | | | |
| ACN (3) | | | | | 5.7 | 0.1 | | | | | | |
| CO | | | 0.0 | 0.0 | 51.4 | 0.6 | 51.4 | 0.9 | 0.0 | 0.0 | 0.0 | 0.0 |
| $CO_2$ | | | 4230.9 | 51.2 | 4482.1 | 51.8 | 4258.0 | 74.0 | 4230.9 | 76.8 | 86.3 | 76.8 |
| $H_2O$ | | | 440.5 | 5.3 | 2439.3 | 28.2 | 460.5 | 8.0 | 440.5 | 8.0 | 9.0 | 8.0 |
| Total | 2751.8 | 100 | 8257.9 | 100 | 8650.8 | 100 | 5756.0 | 100 | 5506.0 | 100 | 112.0 | 100 |

(1) AN = acrylonitrile
(2) ACR = acrolein
(3) ACN = acetonitrile

EXAMPLE IV

A gas mixture comprised of the components listed as feed in TABLE IV was fed into a one-half inch carbon steel reactor containing 5 grams of Pt-Ni/Al$_2$O$_3$ catalyst, sold by United Catalysts Inc. under the designation G#43D. The gas mixture was heated to a temperature of 150° C. and was fed into the reactor at a flow rate of 85 cc/min. The results of this run are tabulated in TABLE IV.

TABLE IV

| Component | Feed cc/min | Feed Vol. % | Effluent cc/min | Effluent Vol % |
|---|---|---|---|---|
| CO$_2$ | 74.80 | 88.00 | 75.66 | 89.52 |
| N$_2$ | 4.67 | 5.5 | 4.67 | 5.53 |
| O$_2$ | 4.25 | 5.0 | 3.64 | 4.31 |
| CO | 0.85 | 1.0 | 0.17 | 0.20 |
| C$_3$H$_6$ | 0.43 | 0.5 | 0.37 | 0.44 |
| Total | 85.0 | 100.00 | 84.51 | 100.00 |

TABLE IV shows that 80 volume percent of the carbon monoxide fed to the reactor was converted to carbon dioxide, while the extent of the hydrocarbon conversion is minimal.

EXAMPLE V

A two stage vapor phase acrylic acid production run was simulated in a fixed bed reactor based on the results obtained in the experiment of EXAMPLE IV. The reactor system was similar to the system of FIG. 2. The simulated feed to the hydrocarbon reactor is comprised of the Fresh Feed component and the Recycle Stream component. The reaction is simulated based on the use of a vapor phase hydrocarbon reactor containing a first fixed catalyst bed of bismuth molybdate and a second fixed bed of mixed molybdenum-tungsten-vanadium catalyst. The system used in this experiment also included a carbon monoxide converter containing a fixed bed of G#43D catalyst. The various flow rates and projected results are tabulated in TABLE V.

Methacrylic acid can be similarly prepared using isobutylene as the hydrocarbon reactant.

scribed in U.S. Pat. No. 4,785,123, the specification of which is incorporated herein by reference. The carbon monoxide oxidation catalyst used in either of Examples I or IV can be used in the process of this experiment.

Although the invention has been described with particular reference to a specific experiment, this experiment is merely exemplary of the invention and variations are contemplated. For example, the reaction can be carried out in the liquid phase or in mixed phases or under other conditions that will effect the production of other petrochemical products. Similarly, other catalysts and adsorbents and other means of gas separation can be used in the invention, if desired. Also, if desired, the product gases leaving the system through line 22 can be further treated, for instance by cryogenic or further adsorptive separation steps, to recover specific components of this stream, such as argon or carbon dioxide.

It is also understood that the invention is not limited to the equipment arrangement illustrated in the drawings. As noted above, the carbon monoxide converter 16 may be positioned upstream of the petrochemical product recovery unit 8, if desired. In fact, it may even be incorporated into reactor 2, either combined with the hydrocarbon oxidation catalyst in the form of a unitary mixed catalyst bed, or alone as a separate bed. If it is incorporated into reactor 2 as a separate bed it is preferably located downstream of the hydrocarbon oxidation catalyst bed. It can be appreciated that the arrangement of the connecting fluid transfer lines for this version of the invention will be different from the arrangement illustrated in the drawings.

The scope of the invention is limited only by the breadth of the appended claims.

We claim:

1. A process for the production of a petrochemical product comprising:
    (a) contacting in a reaction zone a hydrocarbon selected from aromatic hydrocarbons containing 6 to 12 carbon atoms, saturated or ethylenically unsaturated aliphatic or cycloaliphatic hydrocarbons containing 2 to 12 carbon atoms and mixtures of these and an oxygen-containing gas in the presence of a

TABLE V

| Component | Fresh Feed Moles | Fresh Feed % | To Reactor Moles | To Reactor % | Reac. Effluent (1) Moles | Reac. Effluent (1) % | TO CO Conv. Moles | TO CO Conv. % | To Recycle Moles | To Recycle % | To Vent Moles | To Vent % |
|---|---|---|---|---|---|---|---|---|---|---|---|---|
| O$_2$ | 382.6 | 63.59 | 589.1 | 14.8 | 237.2 | 6.00 | 237.2 | 6.73 | 206.5 | 6.01 | 4.2 | 6.01 |
| N$_2$ | 3.86 | 0.64 | 193.2 | 4.78 | 193.2 | 4.89 | 193.2 | 5.48 | 189.4 | 5.51 | 3.9 | 5.51 |
| H$_2$O | | | 137.5 | 3.40 | 366.9 | 9.28 | 141.0 | 4.00 | 137.5 | 4.00 | 2.8 | 4.00 |
| CO | | | 2.8 | 0.07 | 14.2 | 0.36 | 14.2 | 0.40 | 2.8 | 0.08 | 0.1 | 0.08 |
| CO$_2$ | | | 2890.3 | 71.61 | 2922.2 | 73.91 | 2922.5 | 82.89 | 2890.5 | 84.06 | 59.0 | 84.14 |
| Formaldehyde | | | | | 1.5 | 0.04 | | | | | | |
| Formic Acid | | | | | 2.7 | 0.07 | | | | | | |
| Acetaldehyde | | | | | 2.5 | 0.06 | | | | | | |
| Acetic Acid | | | | | 11.4 | 0.29 | | | | | | |
| Propane | | | 7.2 | 0.18 | 7.2 | 0.18 | 9.8 | 0.28 | 6.7 | 0.19 | 0.1 | 0.19 |
| Propylene | 214.7 | 35.69 | 220.0 | 5.44 | 8.8 | 0.22 | 7.7 | 0.22 | 5.3 | 0.15 | 0.1 | 0.15 |
| Acrolein | | | | | 5.3 | 0.13 | | | | | | |
| Acrylic Acid | | | | | 180.8 | 4.57 | | | | | | |
| Propane | 0.5 | 0.08 | | | | | | | | | | |
| Total | 601.6 | 100.0 | 4040.3 | 100.0 | 3954.14 | 100.0 | 3525.6 | 100.0 | 3438.71 | 100.0 | 70.2 | 100.0 |

(1) Two-stage reactor in which propylene is converted to acrolein in the first reactor then further oxidized to acrylic acid in the second reactor.

TABLE V shows that 80 volume percent of the carbon monoxide fed to the reactor was converted to carbon dioxide, while the extent of the hydrocarbon conversion is minimal.

EXAMPLE VI

Propylene oxide can be produced by the reaction of propylene in the presence of a molten salt catalyst comprised of sodium nitrate and potassium nitrate, as dehydrocarbon partial oxidation catalyst and an inert diluent under conditions which produce a gaseous product containing said petrochemical product and carbon monoxide;

(b) removing said petrochemical product from the gaseous product;

(c) partially converting carbon monoxide in the gaseous product to carbon dioxide, thereby producing a carbon monoxide-depleted gas stream;

(d) removing part of the carbon dioxide from the carbon monoxide-depleted gas stream; and (e) recycling the carbon monoxide-depleted gas stream remaining after step (d) to said reaction zone.

2. The process of claim 1 wherein carbon dioxide is present as the principal diluent in the system in which said process is carried out.

3. The process of claim 1 or claim 2 wherein the hydrocarbon is selected from aromatic hydrocarbons containing 6 to 10 carbon atoms and aliphatic hydrocarbons containing 2 to 6 carbon atoms.

4. The process of claim 1 or claim 2, wherein said oxygen-containing gas is substantially pure oxygen.

5. The process of claim 1 or claim 2, wherein said hydrocarbon is a saturated or ethylenically unsaturated hydrocarbon containing 2 to 4 carbon atoms.

6. The process of claim 1, wherein said petrochemical is selected from cyclic anhydrides, nitriles, halogenated hydrocarbons, aldehydes, ethylenically unsaturated carboxylic acids, alkylene oxides and mixture of these.

7. The process of claim 4, wherein said petrochemical product is an ethylenically unsaturated nitrile and said hydrocarbon contains 3 or 4 atoms.

8. The process of claim 7, wherein said petrochemical product is acrylonitrile and said hydrocarbon is propane or propylene.

9. The process of claim 7, wherein said petrochemical product is methacrylonitrile and said hydrocarbon is isobutane or isobutylene.

10. The process of claim 4, wherein said petrochemical product is an alkylene oxide and said hydrocarbon is a straight-chain hydrocarbon containing 2 to 4 carbon atoms.

11. The process of claim 10, wherein said alkylene oxide is propylene oxide and said hydrocarbon is propylene.

12. The process of claim 4, wherein said petrochemical product is an aldehyde and said hydrocarbon is a straight-chain hydrocarbon containing 2 to 4 carbon atoms.

13. The process of claim 12, wherein said petrochemical product is acetaldehyde and said hydrocarbon is ethylene.

14. The process of claim 12, wherein said petrochemical product is acrolein and said hydrocarbon is propylene.

15. The process of claim 4, wherein said petrochemical product is a halogenated hydrocarbon, said hydrocarbon contains 2 to 6 carbon atoms and a hydrogen halide is present in said reaction zone.

16. The process of claim 15, wherein said halogenated hydrocarbon is a chlorinated hydrocarbon, said hydrogen halide is hydrogen chloride.

17. The process of claim 16, wherein said hydrocarbon contains 2 to 4 carbon atoms.

18. The process of claim 17, wherein said petrochemical product is vinyl chloride and said hydrocarbon is ethylene.

19. The process of claim 4, wherein said petrochemical product is an unsaturated carboxylic acid and said hydrocarbon contain 3 or 4 carbon atoms.

20. The process of claim 19, wherein said petrochemical product is acrylic acid and said hydrocarbon is propylene.

21. The process of claim 19, wherein said petrochemical product is methacrylic acid and said hydrocarbon is i-butylene.

22. The process of either of claims 1 or 2, wherein said reaction zone is a reactor selected from the group consisting of fixed bed reactors, fluidized bed reactors, moving bed reactors, trickle bed reactors and transport bed reactors.

23. The process of claim 21, wherein said reactor is a fixed bed reactor.

24. The process of either of claims 1 or 2, wherein the carbon monoxide is converted to carbon dioxide by means of a copper oxide-manganese oxide catalyst or a noble metal catalyst.

25. The process of claim 2, wherein carbon dioxide is separated from said gaseous product by adsorption or absorption.

26. The process of claim 2, wherein the carbon dioxide is separated from said gaseous product by pressure swing adsorption.

27. The process of claim 26, wherein the unit in which said pressure swing adsorption is carried out contains an adsorbent selected form silica gel, molecular sieves and mixtures of these.

28. A process for the production of a petrochemical product selected from cyclic anhydrides, nitriles, halogenated hydrocarbons, aldehydes, carboxylic acids, alkylene oxides and mixtures of these comprising:

(a) contacting in the vapor phase in a reaction zone an aromatic hydrocarbon having 6 to 12 carbon atoms or a saturated or ethylenically unsaturated hydrocarbon having 2 to 12 carbon atoms and an oxygen-containing gas in the presence of a hydrocarbon partial oxidation catalyst and an inert diluent under conditions which produce a gaseous product containing said petrochemical product, unreacted hydrocarbon and carbon monoxide;

(b) removing said petrochemical product from the gaseous product;

(c) converting carbon monoxide in the gaseous product to carbon dioxide, thereby producing a carbon monoxide-depleted stream;

(d) removing at least part of the unreacted hydrocarbon and part of the carbon dioxide from the carbon monoxide-depleted stream; and (d) recycling the removed unreacted hydrocarbon and carbon dioxide to said reaction zone, the carbon dioxide concentration in the recycle stream constituting at least 50 volume percent of the gaseous components present therein.

29. The process of claim 28, wherein carbon dioxide constitutes at least 60 percent of the total volume of gaseous components present in the system in which said process is carried out.

30. A process for the production of a petrochemical product selected form cyclic anhydrides, nitriles, halogenated hydrocarbons, aldehydes, carboxylic acids, alkylene oxides and mixtures of these comprising:

(a) contacting in the vapor phase in a reaction zone an aromatic hydrocarbon having 6 to 12 carbon atoms or a saturated or ethylenically unsaturated hydrocarbon having 2 to 12 carbon atoms and an oxygen-containing gas in the presence of a hydrocarbon partial oxidation catalyst and an inert diluent under conditions which produce a gaseous product containing said petrochemical product, unreacted hydrocarbon and carbon monoxide;

(b) removing said petrochemical product from the gaseous product;

(c) partially converting carbon monoxide in the gaseous product to carbon dioxide, thereby producing a carbon monoxide-depleted stream;

(d) removing at least part of the unreacted hydrocarbon and part of the carbon dioxide from the carbon monoxide-depleted stream; and (e) purging part of the carbon monoxide-depleted gas stream; and (f) recycling the remaining carbon monoxide-depleted gas stream to said reaction zone.

31. The process of claim 1, wherein said petrochemical product is a cyclic anhydride and said hydrocarbon is benzene, orthoxylene, naphthalene or a straight-chain hydrocarbon containing four carbon atoms.

32. The process of claim 31, wherein said cyclic anhydride is maleic anhydride and said hydrocarbon is butane or benzene.

33. The process of claim 31, wherein said cyclic anhydride is phthalic anhydride and said hydrocarbon is orthoxylene.

34. A process for the production of a petrochemical product comprising:

(a) contacting in a reaction zone a hydrocarbon selected from aromatic hydrocarbons containing 6 to 12 carbon atoms, saturated or ethylenically unsaturated aliphatic or cycloaliphatic hydrocarbons containing 2 to 12 carbon atoms and mixtures of these and an oxygen-containing gas in the presence of a hydrocarbon partial oxidation catalyst and an inert diluent under conditions which produce a gaseous product containing said petrochemical product and carbon monoxide;

(b) removing said petrochemical product from the gaseous product;

(c) converting carbon monoxide in the gaseous product to carbon dioxide, thereby producing a carbon monoxide-depleted gas stream;

(d) removing part of the carbon dioxide from the carbon monoxide-depleted gas stream; and (e) recycling the carbon monoxide-depleted gas stream remaining after step (d) to said reaction zone, the carbon dioxide concentration in the recycle stream constituting at least 50 volume percent of the gaseous components present therein.

* * * * *